(12) United States Patent
Witt et al.

(10) Patent No.: US 12,054,295 B2
(45) Date of Patent: Aug. 6, 2024

(54) SYSTEM FOR FILLING CONTAINERS WITH MEDICAL FLUIDS

(71) Applicant: CareFusion 303, Inc., San Diego, CA (US)

(72) Inventors: Erik Witt, Oakland, NJ (US); Jude Cancellieri, Oakland, NJ (US); Ray Isaacson, Layton, UT (US); Ashley Rachel Rothenberg, Morris Plains, NJ (US); Meghan Vellotti, Park Ridge, NJ (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/184,223

(22) Filed: Mar. 15, 2023

(65) Prior Publication Data
US 2023/0219702 A1 Jul. 13, 2023

Related U.S. Application Data
(62) Division of application No. 17/015,929, filed on Sep. 9, 2020, now Pat. No. 11,608,201.
(Continued)

(51) Int. Cl.
*B65B 1/04* (2006.01)
*A61J 1/10* (2006.01)
(Continued)

(52) U.S. Cl.
CPC ............................... *B65B 1/04* (2013.01); *A61J 1/10* (2013.01); *A61J 1/1487* (2015.05); *B65B 3/003* (2013.01);
(Continued)

(58) Field of Classification Search
CPC .. B65B 1/18; B65B 3/17; B65B 3/003; B65B 41/02
(Continued)

(56) References Cited

U.S. PATENT DOCUMENTS 2,259,866 A 10/1941 Stokes
3,599,388 A 8/1971 Feingold
(Continued)

FOREIGN PATENT DOCUMENTS

EP 2731869 A2 5/2014
JP H08509688 A 10/1996
(Continued)

OTHER PUBLICATIONS

International Search Report and Written Opinion for Application No. PCT/US2020/049991, dated Nov. 20, 2020, 14 pages.
(Continued)

*Primary Examiner* — Timothy L Maust
(74) *Attorney, Agent, or Firm* — Morgan, Lewis & Bockius LLP (57) ABSTRACT

Container filling systems are described herein. A container filling system includes a container assembly, a nozzle, a first roller and a second roller. The container assembly includes a plurality of containers, each having a container volume and a fluid manifold defining a fluid pathway, wherein the fluid pathway is in fluid communication with the container volume of each of the plurality of containers. The nozzle is in fluid communication with the fluid pathway, wherein the nozzle directs flow from a fluid source into the fluid pathway. The nozzle separates the fluid manifold into a first portion and a second portion to permit the fluid manifold to advance relative to the nozzle.

20 Claims, 9 Drawing Sheets

Related U.S. Application Data (60) Provisional application No. 62/900,345, filed on Sep. 13, 2019.

(51) Int. Cl.
  *A61J 1/14* (2023.01)
  *B65B 3/00* (2006.01)
  *B65B 3/02* (2006.01)
  *B65B 3/04* (2006.01)
  *B65B 43/12* (2006.01)

(52) U.S. Cl.
  CPC ............... *B65B 3/02* (2013.01); *B65B 3/045* (2013.01); *B65B 43/123* (2013.01)

(58) Field of Classification Search
  USPC .................................. 53/456, 467, 477, 479
  See application file for complete search history.

(56) References Cited

U.S. PATENT DOCUMENTS

| | | |
|---|---|---|
| 3,618,286 A | 11/1971 | Membrino |
| 3,828,833 A | 8/1974 | Smith et al. |
| 4,021,283 A | 5/1977 | Weikert |
| 4,265,279 A | 5/1981 | Weikert |
| 4,893,453 A | 1/1990 | Weikert |
| 5,168,905 A | 12/1992 | Phallen |
| 5,210,993 A | 5/1993 | van Boxtel |
| 5,224,937 A | 7/1993 | van der Heiden et al. |
| 5,327,704 A | 7/1994 | Hoekzema et al. |
| 5,357,733 A * | 10/1994 | Weikert .................. B65B 57/12 53/64 |
| 5,701,937 A | 12/1997 | Bourboulou et al. |
| 6,712,963 B2 | 3/2004 | Schick |
| 7,052,603 B2 | 5/2006 | Schick |
| 9,073,650 B2 * | 7/2015 | Goodwin ................ B65B 51/02 |
| 9,315,281 B2 | 4/2016 | Dissanayake |
| 2002/0083682 A1 | 7/2002 | Edwards et al. |
| 2003/0180486 A1 | 9/2003 | Pape |

FOREIGN PATENT DOCUMENTS

| | | |
|---|---|---|
| JP | 2002513719 A | 5/2002 |
| JP | 2014521405 A | 8/2014 |
| KR | 20170016351 A | 2/2017 |
| WO | WO-2018030096 A1 | 2/2018 |

OTHER PUBLICATIONS

Japanese Office Action for Application No. 2022-516094, dated Mar. 19, 2024, 4 pages including translation.

* cited by examiner

SYSTEM FOR FILLING CONTAINERS WITH MEDICAL FLUIDS

CROSS-REFERENCE TO RELATED APPLICATIONS

The present application is a divisional of U.S. application Ser. No. 17/015,929, filed Sep. 9, 2020, which claims benefit of and priority to U.S. Provisional Patent Application Ser. No. 62/900,345, filed on Sep. 13, 2019, the entirety of which is hereby incorporated herein by reference.

FIELD OF THE INVENTION

The present disclosure generally relates to medical fluid containers, and, in particular, to systems to fill containers with medical fluids.

BACKGROUND

Medical treatments often include the infusion of a medical fluid (e.g., a saline solution, a liquid medication, lipids, blood products, etc.) to patients from a source of fluid, for example, an IV bag or other medical fluid containers. Often, medical fluid containers are filled at a central location and transported to clinical settings, requiring significant resources to transport filled containers.

SUMMARY

In some applications, medical fluid containers are filled locally at decentralized locations, minimizing the transportation of filled containers. However, many decentralized filling systems may be complex and/or may require numerous aseptic fluid connections.

Therefore, in some applications, decentralized filling systems may be unreliable or may have an increased risk of contamination.

The disclosed subject matter relates to container filling systems. In certain embodiments, a container filling system is disclosed that comprises a container assembly, comprising: a plurality of containers, each having a container volume; and a fluid manifold defining a fluid pathway therebetween, wherein the fluid pathway is in fluid communication with the container volume of each of the plurality of containers; a nozzle in fluid communication with the fluid pathway, wherein the nozzle directs flow from a fluid source into the fluid pathway, wherein the nozzle separates the fluid manifold into a first portion and a second portion to permit the fluid manifold to advance relative to the nozzle.

In certain embodiments a method is disclosed that comprises providing a container assembly, comprising: a plurality of containers, each having a container volume; and a fluid manifold defining a fluid pathway, wherein the fluid pathway is in fluid communication with the container volume of each of the plurality of containers; introducing a medical fluid into the fluid pathway via a nozzle; directing the medical fluid into the container volume of a first container of the plurality of containers; advancing the fluid manifold relative to the nozzle; and separating the fluid manifold into a first portion and a second portion after advancing past the nozzle.

In certain embodiments, a container assembly is disclosed that comprises a plurality of containers, each having a container volume; and a fluid manifold defining a fluid pathway therebetween, the fluid manifold comprising a plurality of manifold channels, wherein each of the manifold channels provides fluid communication between the fluid pathway and a respective container of the plurality of containers.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed container filling system incorporates a container assembly with a plurality of containers and a separable fluid manifold in fluid communication with each of the containers. The separable fluid manifold can be separated and advanced as each container is filled and removed while maintaining continuous sterile fluid contact with a filling nozzle. By providing continuous sterile fluid contact with the filling nozzle, the operation of the container filling system can be simplified and the risk of contamination can be minimized.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to filling containers with medical fluid using a separable fluid manifold, it is to be understood that this description is only an example of usage and does not limit the scope of the claims. Various aspects of the disclosed container filling system may be used in any application where it is desirable dispense medical fluid into containers.

The disclosed container filling system overcomes several challenges discovered with respect to certain conventional container filling systems. One challenge with certain conventional decentralized container filling devices is that containers may need to be individually filled to confirm the filled volume. Also, certain decentralized container filling systems may require careful introduction and orientation of the containers into the filling system. Further, certain decentralized container filling systems require numerous connections, each requiring a sterilization process. Because individually loading containers and sterilizing numerous connections may be time consuming and increase the risk of contamination, the use of conventional container filling systems is undesirable.

Therefore, in accordance with the present disclosure, it is advantageous to provide a container filling system as described herein that simplifies the loading and filling of medical fluid containers and eliminates or substantially reduces the risk of contamination. The disclosed container filling system provides a separable fluid manifold can be separated and advanced as each container is filled and removed while maintaining continuous sterile fluid contact with a filling nozzle to simplify the filling of medical containers and to reduce the risk of contamination by minimizing the number of connections made.

An example of a container filling system that simplifies the introduction of medical fluids and reduces the risk of contamination is now described.

Figure 1:
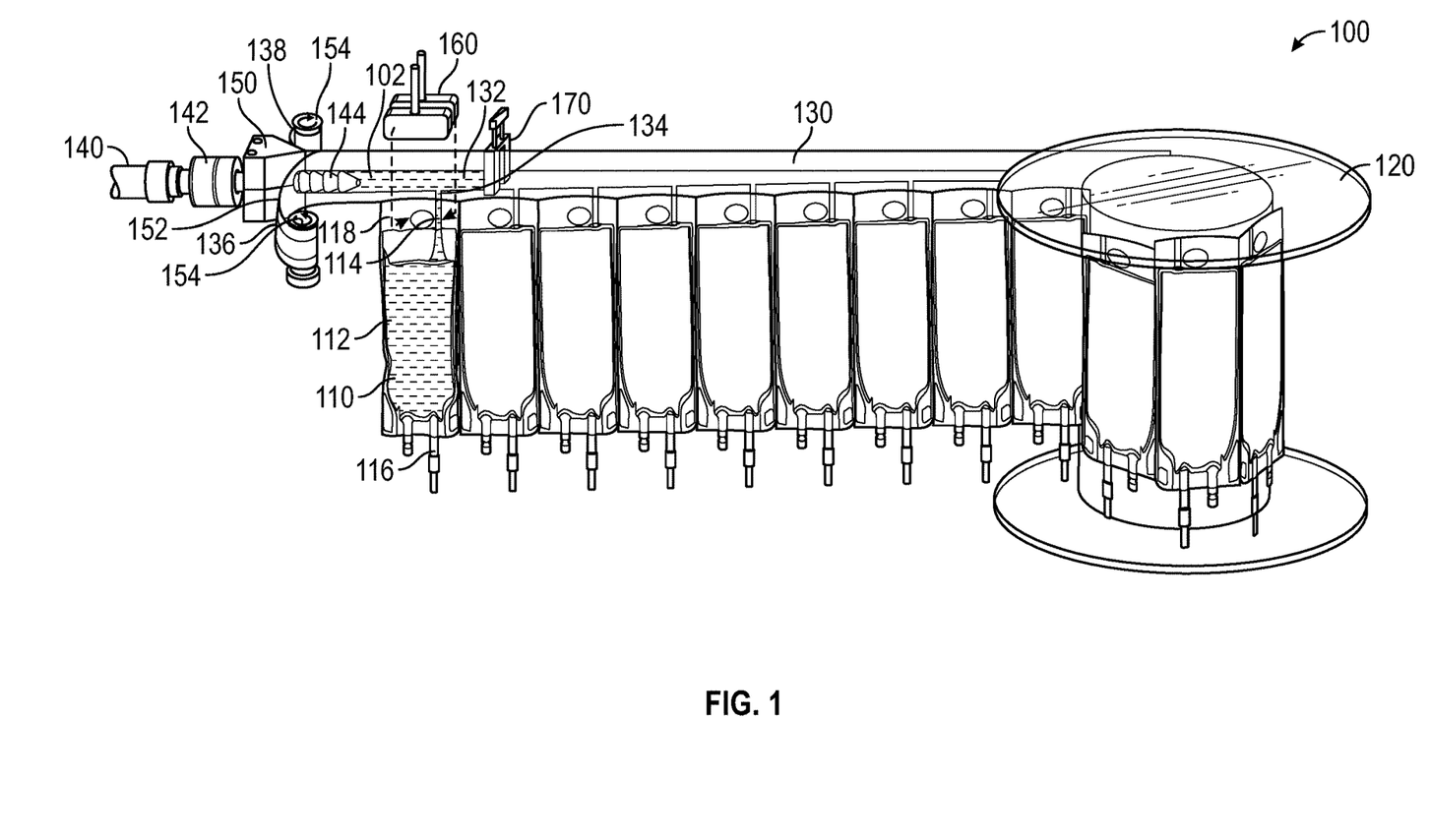
FIG. 1 is a perspective view of a container filling system, in accordance with various aspects of the present disclosure.

FIG. 1 is a perspective view of a container filling system 100, in accordance with various aspects of the present disclosure. In the depicted example, the container filling system 100 continuously fills medical fluid containers 110, such as IV bags, through an aseptic interface. Advantageously, the container filling system 100 allows for sterile or aseptic on-demand filling or sampling of medical fluid containers 110.

In the illustrated embodiment, the container filling system 100 utilizes a container assembly to facilitate the filling of the medical fluid containers 110 and the advancement of the fluid manifold 130. In the depicted example, the container assembly includes a plurality of medical fluid containers 110 that can each be in fluid communication with the fluid manifold 130. As illustrated, each medical fluid container 110 can receive medical fluid from a fluid pathway 132 of the fluid manifold 130. Medical fluid can be directed from the fluid pathway 132 to the medical fluid container 110 via a manifold channel 134 defined for each respective medical fluid container 110. In some embodiments, the medical fluid from the manifold channel 134 is directed into the container volume 112 via a fill port 114 defined in an upper portion 118 of the medical fluid container 110. The container volume 112 can receive, store, and/or dispense medical fluid. Optionally, the upper portion 118 of the medical fluid container 110 can be releasably coupled to the fluid manifold 130. Advantageously, by coupling the medical fluid containers 110 to the fluid manifold 130, the medical fluid containers 110 can be aligned, orientated, and singulated to facilitate handling of the unfilled medical fluid containers 110.

In the illustrated embodiment, the fluid pathway 132 is defined between a separable first film 136 and a second film 138 of the fluid manifold 130. In some embodiments, the top and bottom portions of the first film 136 and the second film 138 are joined, sealed (including heat sealed), or bonded together to define the fluid pathway 132 therebetween. In some embodiments, the bottom portions of the first film 136 and the second film 138 can be joined, sealed (including heat sealed), or bonded together to define the manifold channels 134 that direct fluid flow into each respective medical fluid container 110. As can be appreciated, the fluid manifold 130 may be formed as an integral or singular tubing or manifold and may be separated as described herein. As described herein, the first film 136 and the second film 138 of the fluid manifold 130 can be separated with a wedge device and/or by pulling the first film 136 and the second film 138 apart.

Optionally, the top portion of the fluid manifold 130 can include a ridge or a guide portion to orient the container assembly relative to the container filling system 100. In some embodiments, the guide portion can be received by a guide or track which can extend along a portion of the fluid manifold 130 to keep the fluid manifold 130 level and the unfilled medical fluid containers 110 aligned. In some embodiments, the guide can include a guide frame and can orient and align the container assembly.

As illustrated, the container assembly including the fluid manifold 130 and the unfilled medical fluid containers 110 can be stored on and dispensed from a reel 120. As described herein, as the medical fluid containers 110 are filled and released from the fluid manifold 130 and the fluid manifold 130 is advanced, the reel 120 can dispense remaining unfilled medical fluid containers 110.

Figure 2:
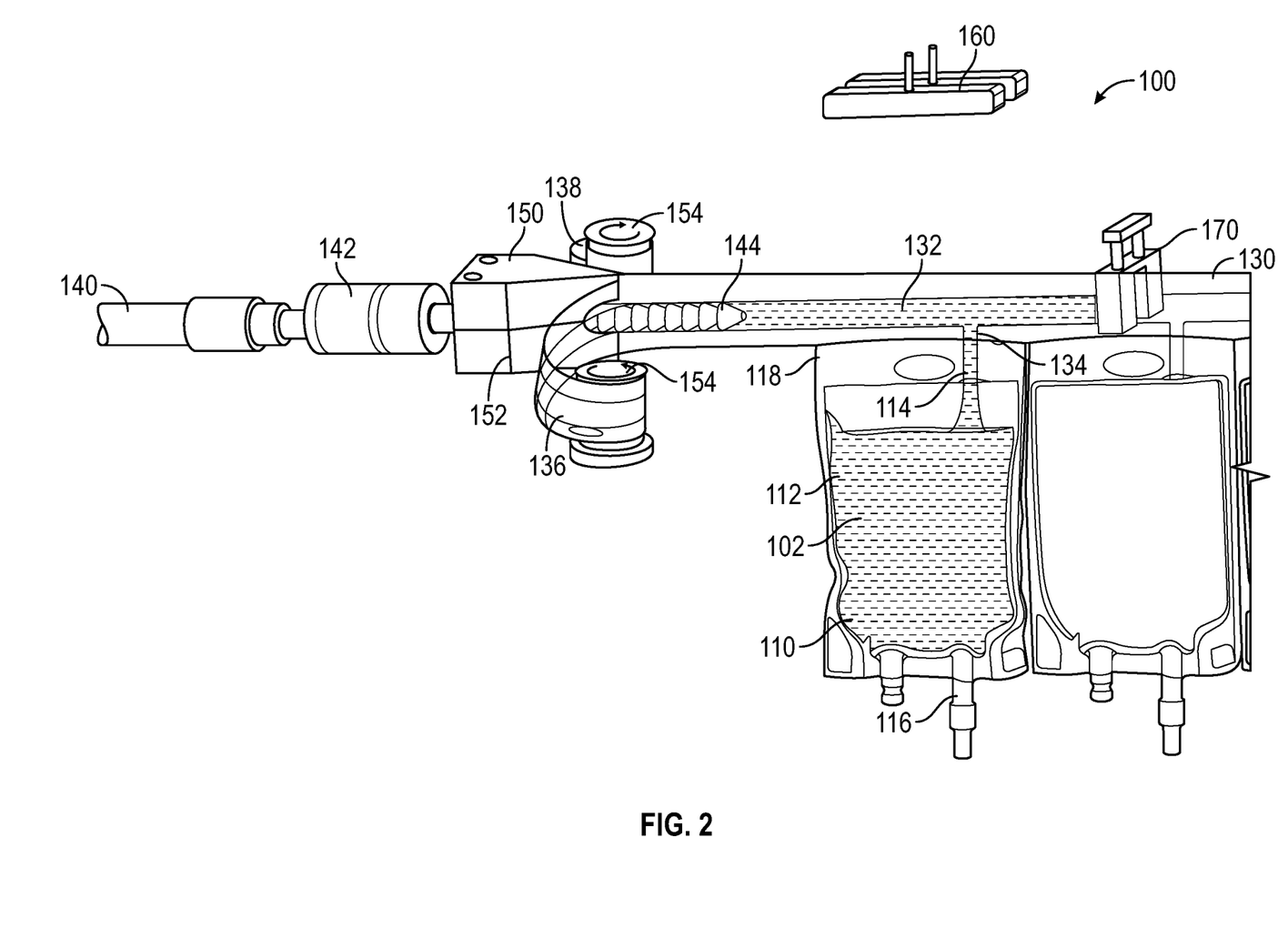
FIG. 2 is a detail view of the container filling system of FIG. 1, in accordance with various aspects of the present disclosure.

FIG. 2 is a detail view of the container filling system 100 of FIG. 1, in accordance with various aspects of the present disclosure. With continued reference to FIGS. 1 and 2, the container filling system 100 directs medical fluid from a medical fluid source 140 into the plurality of medical fluid containers 110. The medical fluid source 140 can provide saline, medication, blood, therapeutics, biosamples, sampled fluids, and/or any other suitable medical fluid. As can be appreciated, any suitable fluid source, including those including non-medical fluids, such as beverages, industrial fluids, or any other fluid can be utilized.

In the illustrated embodiment, a nozzle 142 affixed to the medical fluid source 140 directs medical fluid into the fluid manifold 130. As illustrated, the nozzle end 144 is disposed within the fluid pathway 132, allowing the nozzle 142 to maintain continuous sterile fluid contact with the fluid pathway 132 as the fluid manifold 130 advances. As can be appreciated, the nozzle 142 can be any end portion or port affixed to the medical fluid source 140, and can be converging, diverging, constant radius, or include other geometric features.

During operation, medical fluid from the medical fluid source 140 is introduced into the fluid manifold 130 via the nozzle 142. Medical fluid from the fluid manifold 130 can enter the container volume 112 via the manifold channel 134. In some embodiments, the flow and/or volume of medical fluid directed to a medical fluid container 110 can be metered. Optionally, a fluid clamp 170 can pinch or otherwise constrain the fluid pathway 132 to prevent metered or unmetered medical fluid from entering another unfilled medical fluid container 110 prior to the complete filling of the current medical fluid container 110. In some applications, excess air pressure may be introduced into the fluid manifold 130 as the medical fluid containers 110 are filled. In some embodiments, air pressure within the fluid manifold 130 can be relieved with a fluid pressure regulator and/or a bleed valve.

Optionally, the structure of the nozzle 142 can support the fluid manifold 130 to allow the fluid manifold 130 and the attached medical fluid containers 110 to be aligned during operation.

In some embodiments, the outer diameter of nozzle 142 is sized to provide a seal against the inner diameter of the fluid pathway 132, permitting a continuous seal between the nozzle 142 and the fluid pathway 132 as the fluid manifold 130 advances. As described herein, advantageously, the seal or connection between the nozzle 142 and the fluid pathway 132 does not need to be broken and thus does not need to be re-sterilized. In some embodiments, additional sealing members such as O-rings or elastic bands can be introduced between the nozzle 142 and the fluid pathway 132 to retain a sealing relationship therebetween.

Advantageously, the sealing arrangement of the nozzle 142 with the fluid manifold 130 allows for a single sterile or aseptic connection to be utilized to fill many medical fluid containers 110. Advantageously, the sealing relationship between the nozzle 142 and the fluid manifold 130 can be established in a sterile environment during manufacturing allowing the container filling system 100 to be sterile/aseptic upon arrival to the operating site (e.g. hospital). In some embodiments, components of the container filling system 100 can be terminally sterilized as a unit and packaged as a single consumable, easing loading and packaging requirements. Further, the connection volume that remains aseptic can be small. Optionally, local sterilization techniques such as inductive heating and/or ultraviolet sterilization can be used to sterilize the point of connection.

As described herein, to facilitate filling multiple medical fluid containers 110 while maintaining a sterile sealing interface between the nozzle 142 and the fluid manifold 130, the fluid manifold 130 is advanced relative to the stationary nozzle 142. In the depicted example, the fluid manifold 130 is advanced by takeup mechanisms, devices, or rollers 154.

As illustrated, the first film 136 of the fluid manifold 130 is received and advanced by a roller 154. Similarly, the second film 138 of the fluid manifold 130 is received and advanced by a roller 154. Cooperatively, the rollers 154 advance the fluid manifold 130 past the nozzle 142. In some embodiments, the rollers 154 can include protrusions to engage features of the first and second films 136, 138 to advance the fluid manifold 130. Optionally, the rollers 154 can utilize a pulley system or suction to advance the fluid manifold 130.

In some embodiments, the fluid manifold 130 can be continuously advanced as a medical fluid container 110 is filled or advanced in steps after the medical fluid container 110 is filled. During operation, the rollers 154 can store the portion of the fluid manifold 130 that has been detached from a filled medical fluid container 110. Optionally, the fluid manifold 130 can be pushed toward the nozzle 142 and cut after the filled medical fluid container 110 is detached.

In some embodiments, to facilitate the advancement of the fluid manifold 130, the portion of the fluid manifold 130 advanced past the nozzle 142 can be separated into the first film 136 and the second film 138 to be received by the rollers 154. In the illustrated embodiment, a blade, knife, or wedge 150 disposed along the base portion of the nozzle 142 can separate the fluid manifold 130 into the first film 136 and the second film 138. The wedge surface 152 can be disposed at an angle to initiate and continue the separation of the fluid manifold 130. Optionally, the wedge 150 can be formed from polymer, metal, ceramic, or any other suitable material. In some embodiments, the wedge 150 can be heated to facilitate separation. In some embodiments, the fluid manifold 130 can be separated by the surface of the nozzle 142. Advantageously, by separating the released portion of the fluid manifold 130 into the first film 136 and the second film 138, the filling process can be simplified.

During operation, the nozzle 142 can remain in the fluid pathway 132 as the fluid manifold 130 advances. As can be appreciated, the described configuration minimizes the flow path of the fluid manifold 130 and allows for excess tubing to be stored and retained without interfering with the operation of the container filling system 100. Optionally, the separated first film 136 and second film 138 can joined, sealed (including heat sealed), or bonded together for storage or retention.

Figure 3:
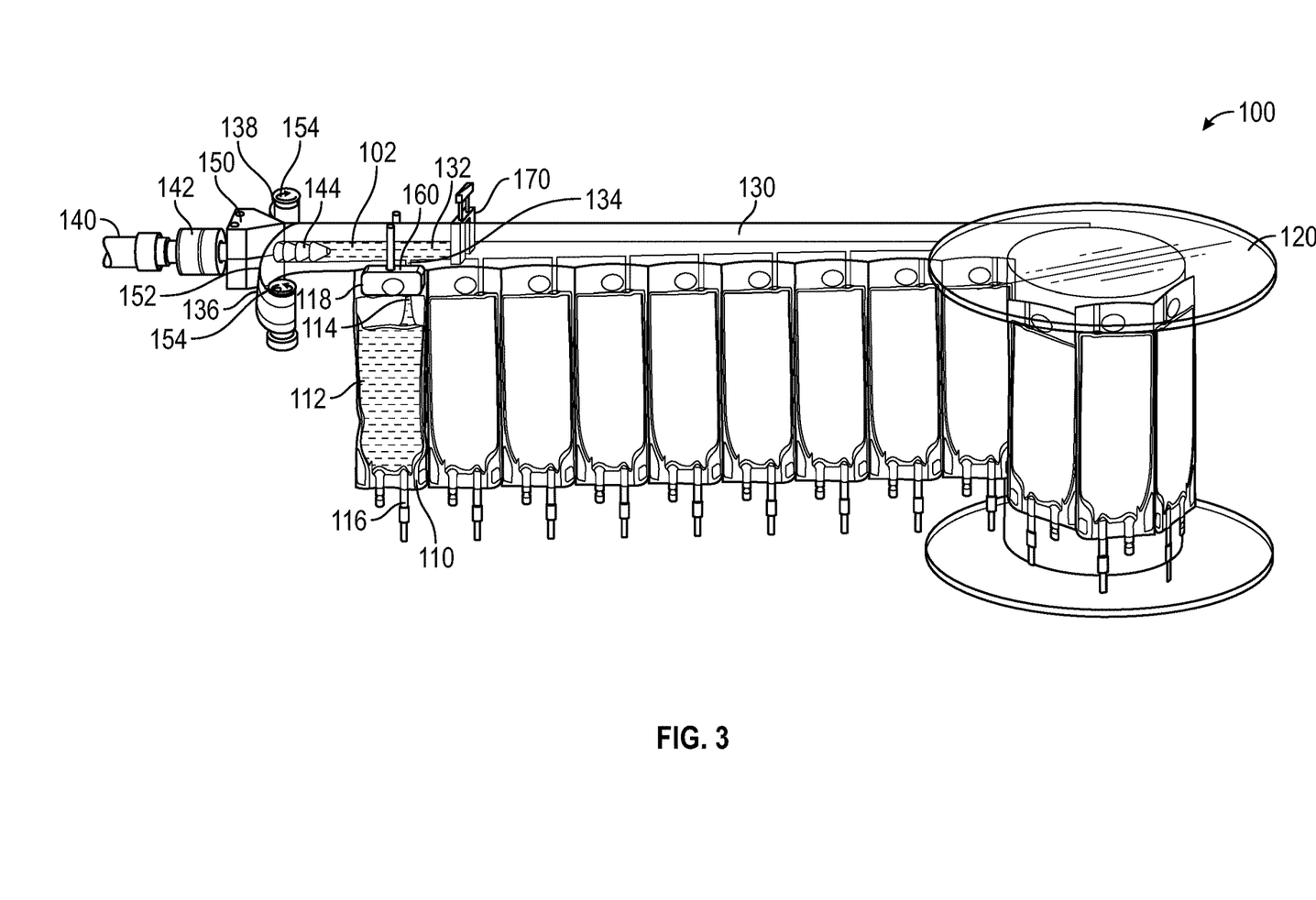
FIG. 3 is a perspective view of the container filling system of FIG. 1 during sealing, in accordance with various aspects of the present disclosure.

FIG. 3 is a perspective view of the container filling system 100 of FIG. 1 during sealing, in accordance with various aspects of the present disclosure. After the desired amount of medical fluid is introduced into the medical fluid container 110, the medical fluid container 110 can be sealed to close the fill port 114 to prepare the medical fluid container 110 for use. As can be appreciated, the volume of medical fluid dispensed to the medical fluid container 110 can be metered by the container filling system 100.

During operation, a heat clamp 160 can apply heat and pressure to the upper portion 118 of the medical fluid container 110 to seal the fill port 114. Optionally, the heat clamp 160 can be configured to apply heat and pressure to the manifold channel 134 to prevent medical fluid within the fluid pathway 132 from inadvertently leaking upon removal of the medical fluid container 110.

Figure 4:
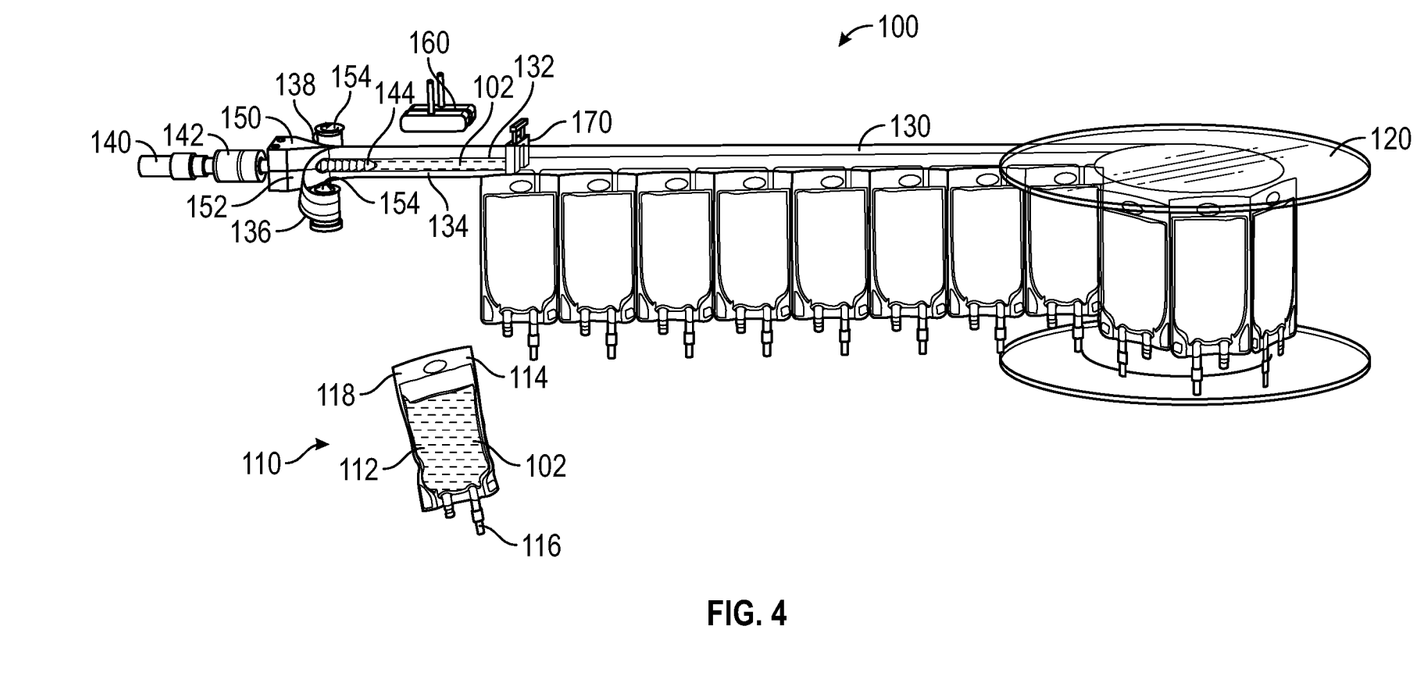
FIG. 4 is a perspective view of the container filling system of FIG. 1 during releasing, in accordance with various aspects of the present disclosure.

FIG. 4 is a perspective view of the container filling system 100 of FIG. 1 during releasing, in accordance with various aspects of the present disclosure. After the medical fluid container 110 is sealed, the medical fluid container 110 can be released from the fluid manifold 130. In some embodiments, the heat clamp 160 can include a cutting element to separate the medical fluid container 110 from the fluid manifold 130. Optionally, the medical fluid container 110 can be configured to separate from the fluid manifold 130 due to the weight of the filled medical fluid container 110.

After the medical fluid container 110 is released, the fluid manifold 130 be advanced to permit the next medical fluid container 110 to be filled. As previously described, the portion of the fluid manifold 130 corresponding to the released medical fluid container 110 can be separated and stored on rollers 154.

After releasing the medical fluid container 110, the medical fluid container 110 can be used in any suitable application. For example, the medical fluid container 110 can be used as an IV bag to permit medical fluid stored within the container volume 112 to be dispensed via fluid port 116.

As can be appreciated, the container filling system 100 and the methods described herein can be utilized in hospitals, clinical care sites, pharmacies, liquid oral medication preparation, and batch IV admixture preparation. The container filling system 100 can allow for exact volume filling of medications and/or mixtures of medications.

Figure 5:
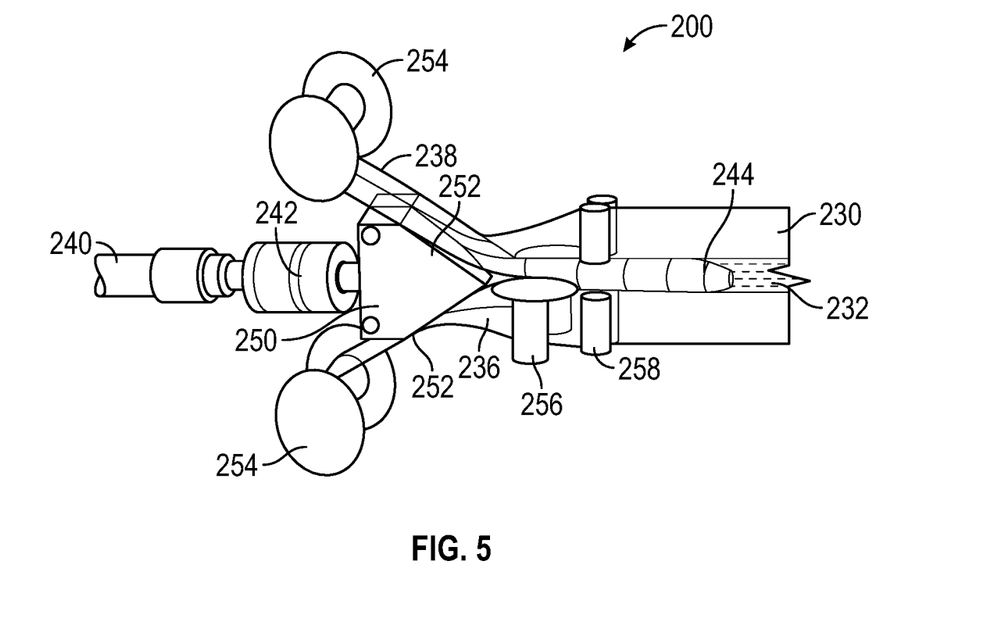
FIG. 5 is a perspective view of a container filling system, in accordance with various aspects of the present disclosure.

FIG. 5 is a perspective view of a container filling system 200, in accordance with various aspects of the present disclosure. In the illustrated embodiment, the container filling system 200 includes features that are similar to features previously discussed with respect to container filling system 100. Except where noted, similar features may be referred to with similar reference numerals and may reference corresponding descriptions.

In some embodiments, the container filling system 200 includes sealing rollers 258 to facilitate sealing the fluid manifold 230 against the nozzle 242. In the depicted example, the sealing rollers 258 can urge portions of the fluid manifold 230 against the nozzle 242. Further, the cutting rollers 256 can separate the top portion and the bottom portion of the first film 236 and the second film 238. In some embodiments, the cutting rollers 256 and the sealing rollers 258 can be urged by biasing members, actuators, or any other suitable mechanism.

Optionally, the wedge 250 can be rotated as needed to accommodate the cutting rollers 256 and the sealing rollers 258. For example, the wedge 250 can be rotated 90 degrees relate to the wedge 150.

Figure 6:
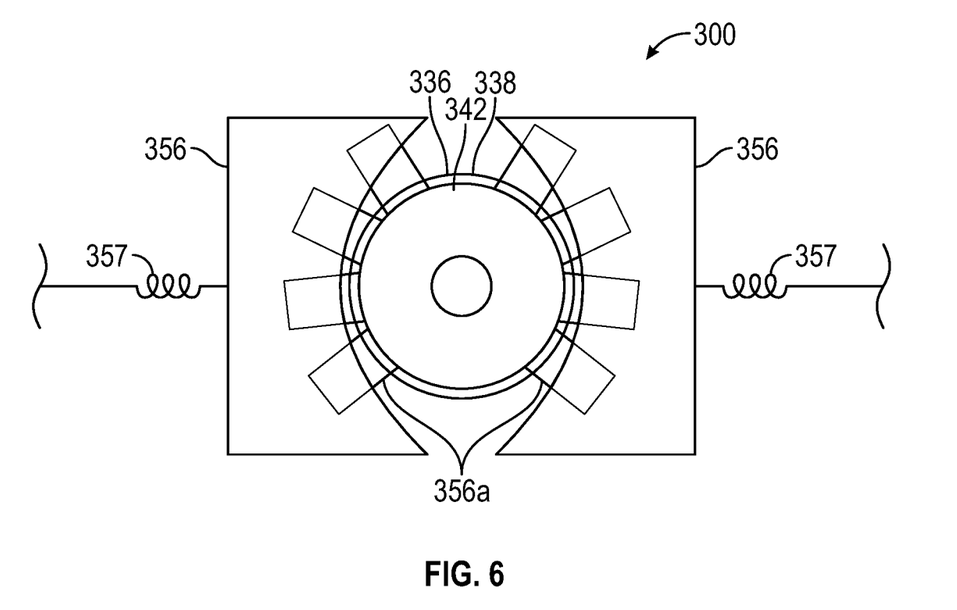
FIG. 6 is a partial cross-sectional view of a container filling system, in accordance with various aspects of the present disclosure.

FIG. 6 is a partial cross-sectional view of a container filling system 300, in accordance with various aspects of the present disclosure. In the illustrated embodiment, the container filling system 300 includes features that are similar to features previously discussed with respect to container filling system 100. Except where noted, similar features may be referred to with similar reference numerals and may reference corresponding descriptions. In the depicted example, the container filling system 300 can include sealing elements 356.

During operation, the fingers 356a extending from the sealing elements 356 radially urge portions of the first film 336 and the second film 338 of the fluid manifold toward the nozzle 342, promoting a seal between the nozzle 342 and the fluid manifold. As can be appreciated, the fingers 356a can be shaped to conform to the round exterior surface of the nozzle 342. In some embodiments, the sealing elements 356 can be urged toward the nozzle 342 with biasing members 357. Optionally, the biasing members 357 can be configured to provide sufficient sealing force without damaging the fluid manifold.

Figure 7:
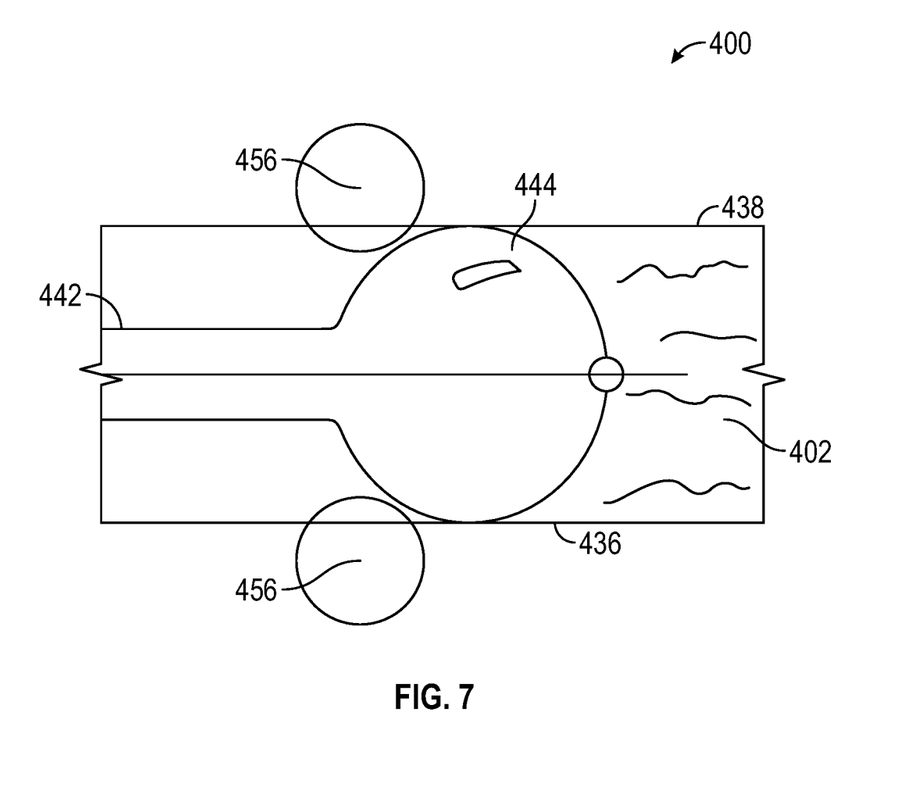
FIG. 7 is a perspective view of a container filling system, in accordance with various aspects of the present disclosure.

FIG. 7 is a perspective view of a container filling system 400, in accordance with various aspects of the present disclosure. In the illustrated embodiment, the container filling system 400 includes features that are similar to features previously discussed with respect to container filling system 100. Except where noted, similar features may be referred to with similar reference numerals and may reference corresponding descriptions.

In some embodiments, the container filling system 400 includes a spherical nozzle 442 to deliver medical fluid to the fluid manifold. As illustrated, the spherical nozzle 442 can include a nozzle end 444 that has a generally spherical shape. The nozzle end 444 can seal against the first film 436 and the second film 438 forming the fluid manifold.

In some embodiments, sealing elements 456 can urge the first film 436 and the second film 438 of the fluid manifold against the exterior surface of the spherical nozzle 442. For example, the sealing elements 456 can urge the fluid manifold against the trailing surface of the spherical nozzle 442. The sealing elements 456 can have a generally round or spherical shape. In some embodiments, the sealing elements 456 can roll as the fluid manifold is advanced.

Figure 8:
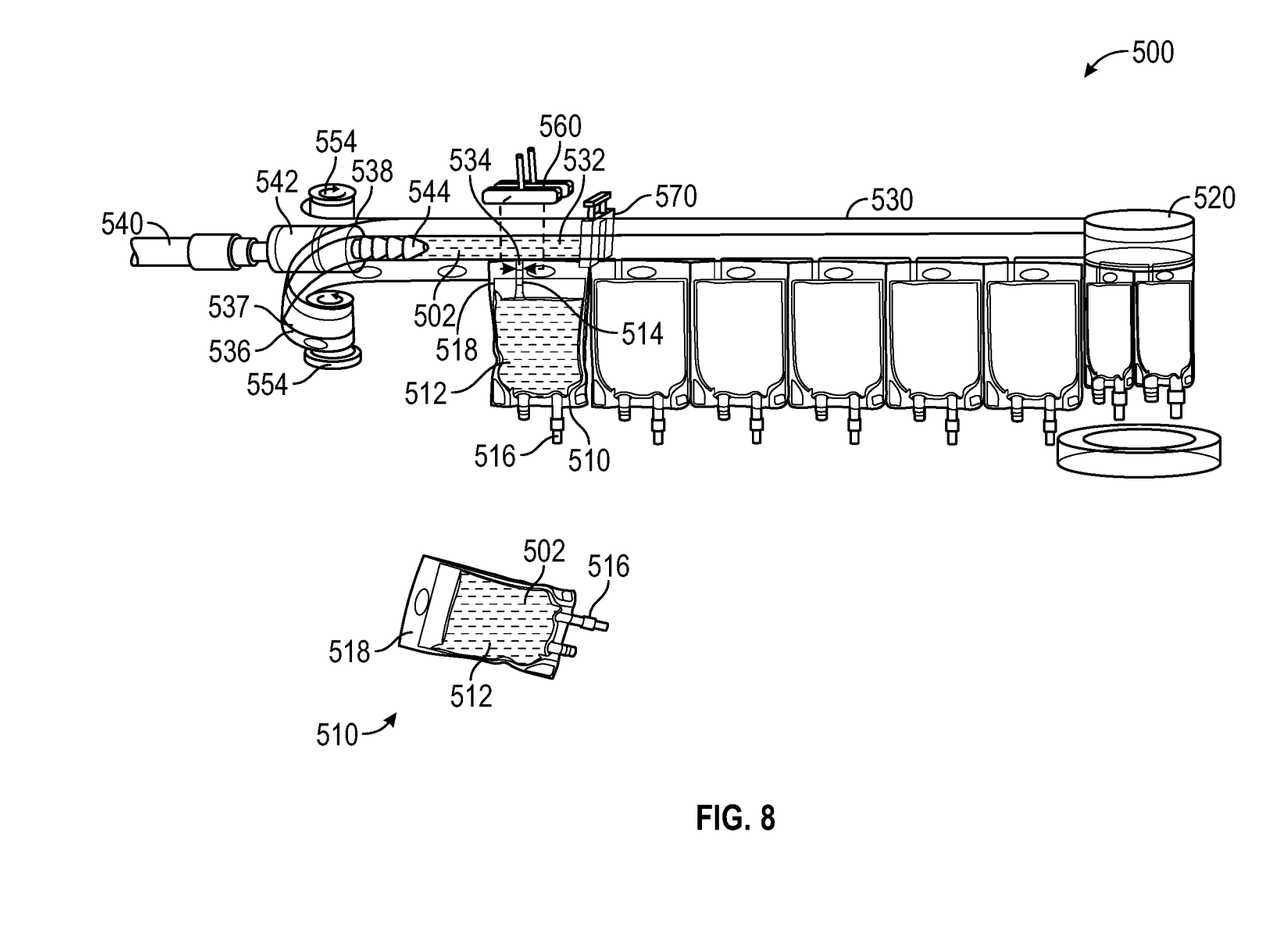
FIG. 8 is a perspective view of a container filling system, in accordance with various aspects of the present disclosure.

FIG. 8 is a perspective view of a container filling system 500, in accordance with various aspects of the present disclosure. In the illustrated embodiment, the container filling system 500 includes features that are similar to features previously discussed with respect to container filling system 100. Except where noted, similar features may be referred to with similar reference numerals and may reference corresponding descriptions.

In the illustrated embodiment, the fluid pathway 532 is defined between a separable first film 536 and a second film 538 of the fluid manifold 530. In the depicted example, the top and bottom portions of the first film 536 and the second film 538 are press fit together to define the fluid pathway 532 therebetween.

Optionally, the nozzle 542 can include sealing elements such as barbs extending from the surface of the nozzle 542 to facilitate or promote sealing between the fluid pathway 532 and the nozzle 542.

In some embodiments, to facilitate the advancement of the fluid manifold 530, the portion of the fluid manifold 530 advanced past the nozzle 542 can be separated into the first film 536 and the second film 538 to be received by the rollers 554. In some embodiments, the fluid manifold 530 can be separated by the surface of the nozzle 542. Optionally, the fluid manifold 530 can be separated by a slider mechanism. Optionally, the separated first film 536 and second film 538 can press fit together for storage or retention.

Figure 9:
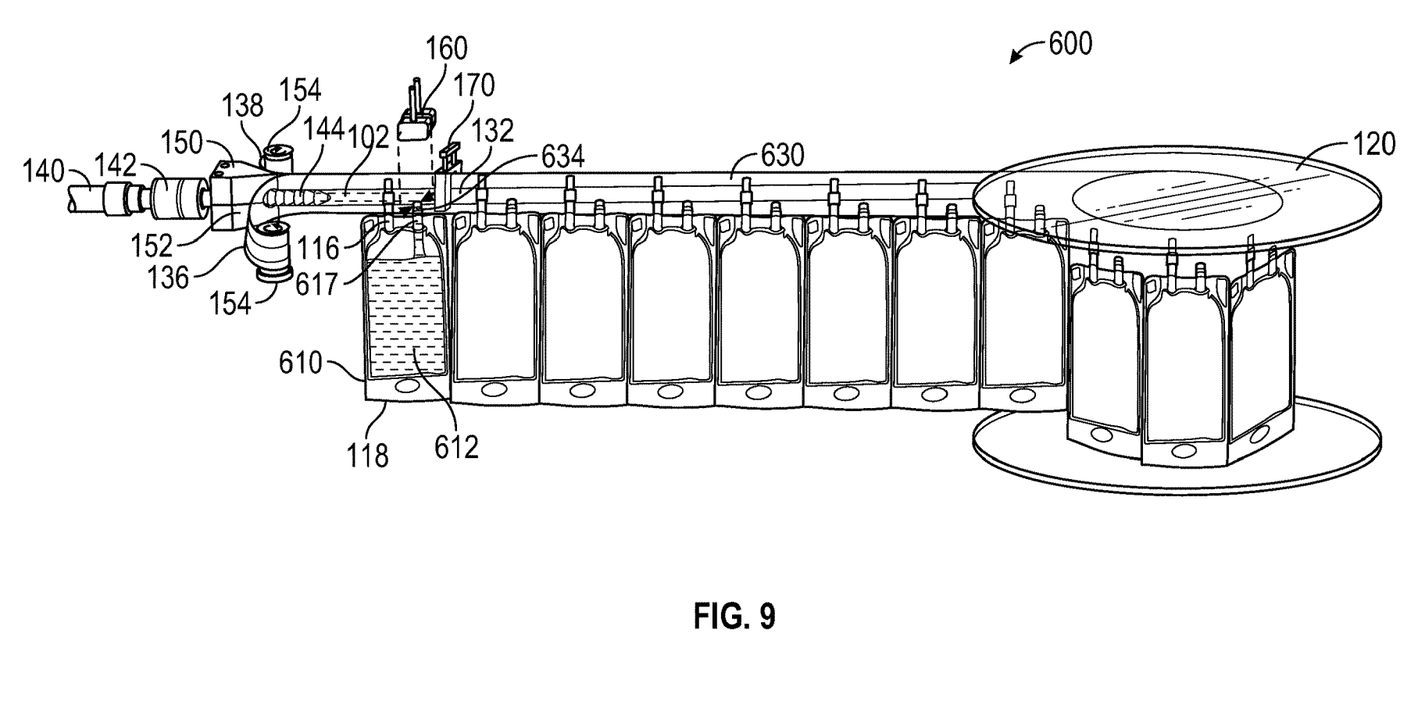
FIG. 9 is a perspective view of a container filling system, in accordance with various aspects of the present disclosure.

FIG. 9 is a perspective view of a container filling system, in accordance with various aspects of the present disclosure. In the illustrated embodiment, the container filling system 600 includes features that are similar to features previously discussed with respect to container filling system 100. Except where noted, similar features may be referred to with similar reference numerals and may reference corresponding descriptions.

In the depicted example, a bottom portion of the medical fluid container 610 can coupled to the fluid manifold 630. By inverting the medical fluid container 610, the medical fluid from the manifold channel 634 is directed into the container volume 612 via a fluid port 617. Advantageously, by utilizing fluid port 617, the medical fluid container 610 does not require a dedicated fill port, simplifying manufacturing of the medical fluid container 610.

Figure 10:
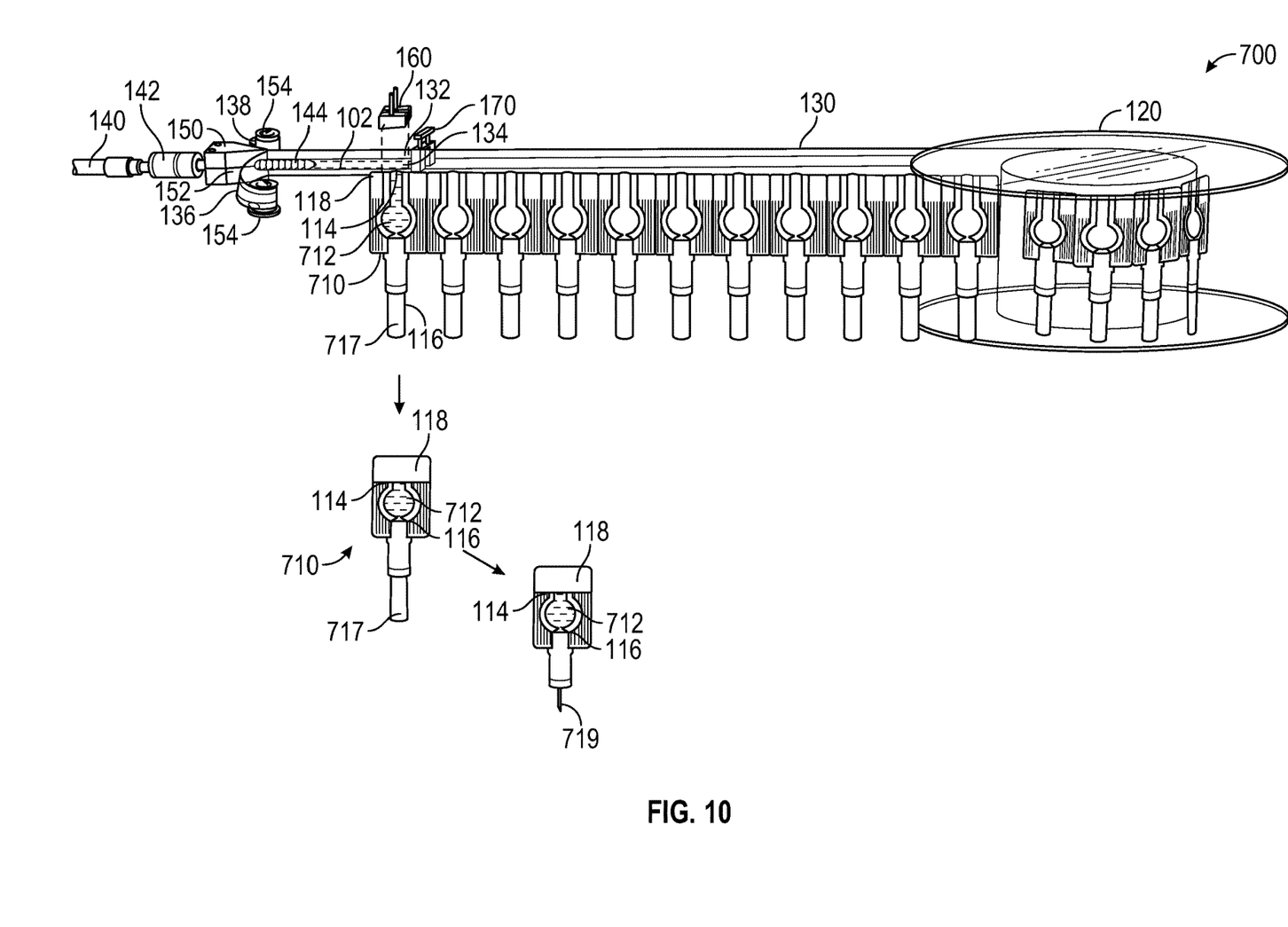
FIG. 10 is a perspective view of a container filling system, in accordance with various aspects of the present disclosure.

FIG. 10 is a perspective view of a container filling system 700, in accordance with various aspects of the present disclosure. In the illustrated embodiment, the container filling system 700 includes features that are similar to features previously discussed with respect to container filling system 100. Except where noted, similar features may be referred to with similar reference numerals and may reference corresponding descriptions.

As can be appreciated, the container filling system 700 can be utilized with any suitable medical fluid container 710, including, but not limited to injection devices, dosing devices, syringes, packets, and/or pouches. As described herein, medical fluid containers 710 can be filled with medical fluids at a decentralized location. After being filled and sealed, the medical fluid containers 710 can be labeled and stored for use. In some embodiments, the cap 717 of the medical fluid container 710 can be removed, exposing a syringe 719 to dispense the medical fluid in the container volume 712.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various examples of aspects of the disclosure are described below as clauses for convenience. These are provided as examples, and do not limit the subject technology.

Clause 1. A container filling system, comprising: a container assembly, comprising: a plurality of containers, each having a container volume; and a fluid manifold defining a fluid pathway, wherein the fluid pathway is in fluid communication with the container volume of each of the plurality of containers; a nozzle in fluid communication with the fluid pathway, wherein the nozzle directs flow from a fluid source into the fluid pathway, wherein the nozzle separates the fluid manifold into a first portion and a second portion to permit the fluid manifold to advance relative to the nozzle.

Clause 2. The container filling system of Clause 1, further comprising a wedge having a wedge surface, wherein the wedge surface is configured to separate the first portion and the second portion.

Clause 3. The container filling system of Clause 1, further comprising a fluid clamp releasably engaged with the fluid manifold, wherein the fluid clamp is configured to direct fluid flow from the fluid pathway to a first container of the plurality of containers.

Clause 4. The container filling system of Clause 1, further comprising a heat clamp releasably engaged with the fluid manifold, wherein the heat clamp is configured to fluidically isolate a first container of the plurality of containers from the fluid pathway.

Clause 5. The container filling system of Clause 1, wherein the first portion and the second portion are releasably bonded.

Clause 6. The container filling system of Clause 1, wherein the first portion and the second portion are releasably press fit.

Clause 7. The container filling system of Clause 1, wherein the fluid manifold comprises a plurality of manifold channels, wherein each of the manifold channels provides fluid communication between the fluid pathway and a respective container of the plurality of containers.

Clause 8. The container filling system of Clause 7, wherein at least one of the manifold channels of the plurality of manifold channels is coupled to a fill port of the respective container.

Clause 9. The container filling system of Clause 7, wherein at least one of the manifold channels of the plurality of manifold channels is coupled to a dispensing port of the respective container.

Clause 10. The container filling system of Clause 1, wherein the plurality of containers comprises a plurality of IV bags.

Clause 11. The container filling system of Clause 1, wherein the plurality of containers comprises a plurality of injection devices.

Clause 12. The container filling system of Clause 1, wherein the fluid manifold comprises a guide ridge disposed opposite to the plurality of containers.

Clause 13. The container filling system of Clause 1, further comprising a sealing member coupled to the nozzle, wherein the sealing member engages between the fluid pathway and the nozzle.

Clause 14. The container filling system of Clause 1, further comprising a sealing member disposed adjacent to the nozzle, wherein the sealing member is configured to urge the fluid manifold against the nozzle.

Clause 15. A method, comprising: providing a container assembly, comprising: a plurality of containers, each having a container volume; and a fluid manifold defining a fluid pathway, wherein the fluid pathway is in fluid communication with the container volume of each of the plurality of containers; introducing a medical fluid into the fluid pathway via a nozzle; directing the medical fluid into the container volume of a first container of the plurality of containers; advancing the fluid manifold relative to the nozzle; and separating the fluid manifold into a first portion and a second portion after advancing past the nozzle.

Clause 16. The method of Clause 15, further comprising: sealing the container volume of the first container from the fluid pathway.

Clause 17. The method of Clause 16, further comprising: releasing the first container from the fluid manifold.

Clause 18. The method of Clause 17, further comprising: directing the medical fluid into the container volume of a second container of the plurality of containers.

Clause 19. The method of Clause 15, further comprising metering a desired volume of medical fluid into the container volume of the first container.

Clause 20. A container assembly, comprising: a plurality of containers, each having a container volume; and a fluid manifold defining a fluid pathway, the fluid manifold comprising a plurality of manifold channels, wherein each of the manifold channels provides fluid communication between the fluid pathway and a respective container of the plurality of containers.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A container assembly, comprising:
a plurality of containers, each having a container volume; and
a fluid manifold comprising a separable first and second film coupled to collectively define a fluid pathway, wherein the fluid pathway is in fluid communication with the container volume of each of the plurality of containers, and the separable first and second film are configured to separate into a first and second portion that are both separate from the plurality of containers without cutting the separable first and second film.

2. The container assembly of claim 1, wherein the first film and the second film are releasably bonded.

3. The container assembly of claim 1, wherein the first film and the second film are releasably press fit.

4. The container assembly of claim 1, wherein each respective container defines a fill port.

5. The container assembly of claim 1, wherein each respective container defines a dispensing port.

6. The container assembly of claim 1, wherein the plurality of containers comprises a plurality of IV bags.

7. The container assembly of claim 1, wherein the separable first and second film are configured to separate into the first portion consisting of a portion of the first film and the second portion consisting of a portion of the second film that are both separate from the plurality of containers.

8. The container assembly of claim 2, further comprising a bond material coupling the first and second film, wherein the bond material is configured to release and separate the first and second film, and the bond material is different than a material of the first and second film.

9. A container assembly, comprising:
a plurality of containers, each having a container volume; and
a fluid manifold comprising:
a separable first and second film coupled to collectively define a fluid pathway, wherein the separable first and second film are configured to separate into a first portion consisting of a portion of the first film and a second portion consisting of a portion of the second film that are both separate from the plurality of containers without cutting the separable first and second film; and
a plurality of manifold channels, wherein each of the manifold channels provides fluid communication between the fluid pathway and a respective container of the plurality of containers.

10. The container assembly of claim 9, wherein at least one of the manifold channels of the plurality of manifold channels is coupled to a fill port of the respective container.

11. The container assembly of claim 9, wherein at least one of the manifold channels of the plurality of manifold channels is coupled to a dispensing port of the respective container.

12. The container assembly of claim 9, wherein the first film and the second film are releasably bonded.

13. The container assembly of claim 9, wherein the first film and the second film are releasably press fit.

14. The container assembly of claim 9, wherein the plurality of containers comprises a plurality of IV bags.

15. The container assembly of claim 9, further comprising a bond material coupling the first and second film, wherein the bond material is configured to release and separate the first and second film, and the bond material is different than a material of the first and second film.

16. A container assembly, comprising:
a plurality of containers, each having a container volume, a fill port and a dispensing port; and
a fluid manifold comprising:
a separable first and second film coupled to collectively define a fluid pathway, wherein the separable first and second film are configured to separate into a first portion consisting of a portion of the first film and a second portion consisting of a portion of the second film that are both separate from the plurality of containers without cutting the separable first and second film; and a plurality of manifold channels, wherein each of the manifold channels provides fluid communication between the fluid pathway and a respective container of the plurality of containers.

17. The container assembly of claim 16, wherein at least one of the manifold channels of the plurality of manifold channels is coupled to the fill port of the respective container.

18. The container assembly of claim 16, wherein at least one of the manifold channels of the plurality of manifold channels is coupled to the dispensing port of the respective container.

19. The container assembly of claim 16, wherein the plurality of containers comprises a plurality of IV bags.

20. The container assembly of claim 16, wherein the first portion and the second portion are pre-defined.

* * * * *